United States Patent [19]

Chopdekar et al.

[11] Patent Number: 5,442,092

[45] Date of Patent: Aug. 15, 1995

[54] PREPARATION OF ESTERS OF 3,5,6-TRICHLOROSALICYCLIC ACID

[75] Inventors: Vilas M. Chopdekar, Edison; James R. Schleck, Somerset, both of N.J.

[73] Assignee: Jame Fine Chemicals, Inc., Bound Brook, N.J.

[21] Appl. No.: 222,400

[22] Filed: Apr. 4, 1994

[51] Int. Cl.⁶ .............................................. C07C 69/76
[52] U.S. Cl. ...................................................... 560/65
[58] Field of Search ........................................... 560/65

[56] References Cited

U.S. PATENT DOCUMENTS 3,706,774  12/1972  Gitlitz .............................. 260/429.7
5,194,666  3/1993  Sedlak et al. ........................ 560/62

OTHER PUBLICATIONS

D. M. Puri et al. "Ethylene Glycol Derivatives of Titanium", Indian J. Chem. vol. 5, Sep., 1967 pp. 448–450.

*Primary Examiner*—Paul J. Killos
*Attorney, Agent, or Firm*—Jack Matalon

[57] ABSTRACT

An improved process for the preparation of esters of 3,5,6-trichlorosalicylic acid which comprises reacting the acid with an alcohol under distillation conditions in the presence of a catalyst comprising a glycol titanate or glycol stannate. The process results in substantially quantitative yields of the ester without any significant side reactions, e.g. conversion of the alcohol to by-product ether.

18 Claims, No Drawings

PREPARATION OF ESTERS OF 3,5,6-TRICHLOROSALICYCLIC ACID

FIELD OF THE INVENTION

The present invention relates to a process for preparing esters of 3,5,6-trichlorosalicylic acid. More particularly, the invention relates to a process for preparing such esters using as the catalyst therefor, a glycol titanate or stannate.

BACKGROUND OF THE INVENTION

Esters of 3,5,6-trichlorosalicylic acid are quite useful as components of formulations which produce light by a chemiluminescent reaction. Various prior art processes exist for preparing such esters such as are described in U.S. Pat. No. 5,194,666. These prior art processes utilize acid esterification catalysts such as sulfuric acid and p-toluenesulfonic acid to bring about the esterification of the 3,5,6-trichlorosalicylic acid with a $C_3$–$C_{20}$ alcohol such as n-pentanol in the presence of an aromatic solvent such as xylene. The principal disadvantage of such prior art processes is that a significant amount of the alcohol is converted to by-product ether due to a competing etherification reaction.

The '666 patent is directed towards an improvement in the prior art esterification processes in that it virtually excludes the competing etherification reaction by substituting a titanium ester or titanium chelate or mixtures thereof for the acid catalysts. The titanium esters disclosed in the '666 patent are tetralkyl titanates, preferably those embraced by the general formula $(R'O)_4Ti$, wherein the $R'$ groups are independently $C_2$–$C_{10}$ alkyl groups such as tetraisopropyl titanate or tetra-n-butyl titanate. The titanium chelates disclosed in the '666 patent include titanium acetonyl acetonate chelate and titanium ethyl acetoacetate chelate.

Although the titanium esters and titanium chelates employed as esterification catalysts in the '666 patent appear to be effective in esterifying 3,5,6-trichlorosalicylic acid without a significant production of by-product ether, they are nevertheless disadvantageous in comparison to the materials employed in the present invention. The glycol titanates and stannates employed as catalysts herein for the esterification of 3,5,6-trichlorosalicylic acid may be utilized in significantly lower quantities than the esterification catalysts employed in the '666 patent. Moreover, the esterification process of the present invention entails a reaction time which is radically shorter than that of the '666 patent. The smaller quantity of catalyst and shorter reaction time with virtually no ether by-product formation results in considerable savings in manufacturing costs for the instant process as compared to that of the '666 patent.

DETAILS OF THE INVENTION

The present invention pertains to a process for preparing esters of 3,5,6-trichloro-salicylic acid which comprises:

a) preparing a reaction mixture comprising 3,5,6-trichlorosalicylic acid, a solvent and about 100–175 mol %, based on said acid, of a $C_1$–$C_{20}$ straight or branched chain alcohol and a catalytic amount of a catalyst selected from the group consisting of glycol titanates and glycol stannates; and b) heating the mixture and distilling off water from the mixture until substantially all the water has been removed.

It should be noted that the terms "glycol titanate" and "glycol stannate" and "stannous glycoloxide" may be referred to in the prior art or as titanium glycoxide or stannous glycoxide or as alkylene glycol titanate, alkylene glycol stannate, titanium alkylene glycolate, etc. Regardless of the nomenclature employed in the prior art, the glycol titanates and glycol stannates employed in the present invention are known materials.

The glycol titanates and glycol stannates employed as esterification catalysts in the present invention are those wherein the glycol moiety contains 2 to 8 carbon atoms, preferably 2 to 5 carbon atoms. The most useful glycol titanates and glycol stannates are those prepared by the reaction of a titanium alkoxide or stannous oxide (hydrous or anhydrous form) and an alkylene glycol such as ethylene glycol, 1,2-propanediol, 1,3-propanediol, 1,4-butanediol, and the like. The preferred esterification catalysts are ethylene glycol titanate and ethylene glycol stannate.

Ethylene glycol titanate is a known material; it has a CAS Registry No. of 310-92-9 and is referred to as titanate ethylene glycoloxide; titanium ethylene glycolate; 1,2-ethanediol, titanium complex; ethylene titanate-(IV) (7CI); titanium, bis[1,2-ethanediolato(2-)-O,O']-, (T-4)- (9CI); 1,4,6,9-tetraoxa-5-titanspiro[4.4]nonane (8CI) and the like. The article entitled "Ethylene Glycol Derivatives of Titanium" by D. M. Purl and R. C. Mehrotra in *Indian J. Chem.*, vol.5, September, 1967, pp. 448–450 and the references cited therein provide information on the preparation of such material (referred to as titanium diethylene glycollate in such article); such article is incorporated by reference herein.

The glycol stannates are well known materials and may be prepared by the process described in U.S. Pat. No. 3,706,774 which is incorporated herein by reference.

The glycol titanates or stannate catalysts are employed in amounts of about 0.1–5, preferably 0.5–3, wt. %, based on the weight of the 3,5,6-trichlorosalicylic acid. The alcohol employed in the esterification of the 3,5,6-trichlorosalicylic acid comprises a $C_1$–$C_{20}$ straight or branched chain alcohol. Preferably, the alcohol is a $C_2$–$C_8$ straight chain alcohol, e.g. ethanol, n-propanol, n-butanol, n-pentanol, n-hexanol, and the like. The particularly preferred alcohol is n-pentanol. The alcohol is employed in an amount of about 100–175 mol %, preferably 130–160 mol %, based on the acid.

The solvent for the reaction mixture preferably is a $C_6$–$C_{10}$ aromatic hydrocarbon. Useful hydrocarbons are ortho-, meta- or para-xylene; mixtures of such xylenes; c) toluene; and d) mixtures of at least one isomer of xylene and toluene. Typically, the solvent is utilized in an amount of 1–8, preferably 3–6, parts by weight per part (by weight) of the alcohol employed to esterify the 3,5,6-trichlorosalicylic acid.

The esterification process is simple to carry out and proceeds very rapidly by using the titanium or stannous glycoloxide catalysts. After preparing the reaction mixture of the 3,5,6-trichlorosalicylic acid, alcohol, solvent and glycol titanate or stannate, the mixture is heated at a temperature of about 120°–150° C. and substantially all the water formed during the esterification reaction is azeotropically distilled off. The ester is thereafter recovered by stripping off the solvent and excess unreacted alcohol.

The following nonlimiting examples serve to illustrate the invention. Unless otherwise indicated, all parts are by weight.

EXAMPLES 1-4

In the following examples, the laboratory equipment consisted of a three-neck flask fitted with a stirrer, thermometer, condenser and Dean-Stark trap. In each example, 100 g 3,5,6-trichlorosalicylic acid, 56 g n-pentyl alcohol, and 300 g xylene (mixed isomers) were charged to the flask. The mixture was heated to 136° C. and held at such temperature for one hour in order to remove any trace moisture in the acid, alcohol and/or solvent. The mixture was then cooled to 120° C. and the catalyst in the amount indicated in Table I was added. The reaction mixture was heated to about 136° C. and the water formed during the esterification reaction was azeotropically distilled off and heating was continued for the indicated time.

At the end of the indicated reaction time, the heating was discontinued and the amount of reaction water azeotropically distilled off was measured and recorded as a percentage of the calculated amount of reaction water. In addition the contents of the flask were checked by GC and HPLC and found to be free of unreacted 3,5,6-trichlorosalicylic acid and any pentyl ether by-product. The solvent and excess unreacted alcohol were then stripped off using a rotary evaporator and the yield of the pentyl ester of 3,5,6-trichlorosalicylic acid was determined to be in excess of 97% for each example.

TABLE I

| Ex. | Catalyst Type | Catalyst* | Reaction Time, hrs. | Reaction Water, % | By-product Ether |
|---|---|---|---|---|---|
| 1 | TIPT[1] | 5 wt. % | 6.5 | 102 | Trace |
| 2 | EGT[2] | 0.5 wt. % | 14 | 100.7 | Trace |
| 3 | EGT[2] | 1 wt. % | 6.5 | 102 | Trace |
| 4 | EGT[2] | 2 wt. % | 3 | 103 | Trace |

*based on the weight of 3,5,6-trichlorosalicylic acid
[1] tetraisopropyltitanate as per U.S. Pat. No. 5,194,666
[2] ethylene glycol titanate

EXAMPLE 5

Example 1 was repeated using concentrated sulfuric acid (97%), in an amount of 5 wt. %, based on the weight of 3,5,6-trichlorosalicylic acid, as the catalyst instead of TIPT. The reaction mixture was heated at reflux (~136° C.) for 40 hours, and the remainder of the procedure was identical to that employed in Example 1. The yield of the pentyl ester of 3,5,6-trichlorosalicylic acid was only 70% and an assay based on GC and HPLC indicated that a very significant amount of by-product pentyl ether had been formed.

EXAMPLE 6

Example 1 was repeated using stannous oxalate in an amount of 5 wt. %, based on the weight of 3,5,6-trichlorosalicylic acid, as the catalyst instead of TIPT. The reaction mixture was heated at reflux (~136° C.) for 72 hours, and the remainder of the procedure was identical to that employed in Example 1. The yield of the pentyl ester of 3,5,6-trichlorosalicylic acid was only 55% and an assay based on GC and HPLC indicated that a very significant amount of by-product pentyl ether had been formed.

EXAMPLE 7

Example 1 was repeated using ethylene glycol stannate in an amount of 2 wt. %, based on the weight of 3,5,6-trichloro-salicylic acid, as the catalyst instead of TIPT. The reaction mixture was heated at reflux (~136° C.) for 13 hours, and the remainder of the procedure was identical to that employed in Example 1. The yield of the pentyl ester of 3,5,6-trichlorosalicylic acid was 96.5% and an assay based on GC and HPLC indicated that no by-product pentyl ether had been formed.

What is claimed is:

1. A process for preparing esters of 3,5,6-trichlorosalicylic acid which comprises:
    a) preparing a reaction mixture comprising 3,5,6-trichlorosalicylic acid, a solvent and about 100-175 mol %, based on said acid, of a $C_1$-$C_{20}$ straight or branched chain alcohol and a catalytic amount of a catalyst selected from the group consisting of glycol titanates and glycol stannates; and
    b) heating the mixture and distilling off water from the mixture until substantially all the water has been removed.

2. The process of claim 1 wherein the alcohol comprises a $C_2$-$C_8$ straight chain alcohol.

3. The process of claim 2 wherein the alcohol comprises n-pentanol.

4. The process of claim 1 wherein the catalyst is present in an amount of about 0.1 to 5 wt. %, based on said acid.

5. The process of claim 1 wherein the solvent comprises at least one $C_6$-$C_{10}$ aromatic hydrocarbon.

6. The process of claim 5 wherein the hydrocarbon is selected from the group consisting of a) ortho-, meta- or para-xylene; b) mixtures of ortho-, meta- and para-xylenes; c) toluene; and d) mixtures of at least one isomer of xylene and toluene.

7. A process for preparing esters of 3,5,6-trichlorosalicylic acid which comprises:
    a) preparing a reaction mixture comprising 3,5,6-trichlorosalicylic acid, a solvent and about 100-175 mol %, based on said acid, of a $C_1$-$C_{20}$ straight or branched chain alcohol and a catalytic amount of a catalyst comprising a glycol titanate; and
    b) heating the mixture and distilling off water from the mixture until substantially all the water has been removed.

8. The process of claim 7 wherein the alcohol comprises a $C_2$-$C_8$ straight chain alcohol.

9. The process of claim 8 wherein the alcohol comprises n-pentanol.

10. The process of claim 7 wherein the catalyst is present in an amount of about 0.1 to 5 wt. %, based on said acid.

11. The process of claim 7 wherein the glycol moiety in the glycol titanate catalyst contains 2 to 8 carbon atoms.

12. The process of claim 11 wherein the catalyst comprises ethylene glycol titanate.

13. A process for preparing esters of 3,5,6-trichlorosalicyclic acid which comprises:
    a) preparing a reaction mixture comprising 3,5,6-trichlorosalicyclic acid, a solvent and about 100-175 mol %, based on said acid, of a $C_1$-$C_{20}$ straight or branched chain alcohol and a catalytic amount of a catalyst comprising a glycol stannate; and b) heating the mixture and distilling off water from the mixture until substantially all the water has been removed.

14. The process of claim 13 wherein the alcohol comprises a $C_2$–$C_8$ straight chain alcohol.

15. The process of claim 14 wherein the alcohol comprises n-pentanol

16. The process of claim 13 wherein the catalyst is present in an amount of about 0.1 to 5 wt. %, based on said acid.

17. The process of claim 13 wherein the glycol moiety in the glycol stannate catalyst contains 2 to 8 carbon atoms.

18. The process of claim 17 wherein the catalyst comprises ethylene glycol stannate.

* * * * *